(12) United States Patent
Song et al.

(10) Patent No.: US 6,924,291 B2
(45) Date of Patent: Aug. 2, 2005

(54) PROCESS FOR MAKING SPIRO ISOBENZOFURANONE COMPOUNDS

(75) Inventors: Zhiquo Jake Song, Edison, NJ (US); Matthew Mangzhu Zhao, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 393 days.

(21) Appl. No.: 10/054,413

(22) Filed: Jan. 22, 2002

(65) Prior Publication Data

US 2002/0151456 A1 Oct. 17, 2002

Related U.S. Application Data

(60) Provisional application No. 60/263,463, filed on Jan. 23, 2001.

(51) Int. Cl.[7] .............................................. A61K 31/44
(52) U.S. Cl. ........................ 514/278; 514/409; 514/407; 514/397; 514/314; 514/302; 514/275; 514/253.01
(58) Field of Search ................................ 514/278, 409, 514/407, 397, 314, 302, 275, 253.01, 253

(56) References Cited

U.S. PATENT DOCUMENTS

| | | |
|---|---|---|
| 6,191,160 B1 | 2/2001 | Gao et al. |
| 6,313,298 B1 | 11/2001 | Gao et al. |
| 6,326,375 B1 | 12/2001 | Fukami et al. |
| 6,335,345 B1 | 1/2002 | Fukami et al. |
| 6,649,624 B2 * | 11/2003 | Fukami et al. ............... 514/278 |

FOREIGN PATENT DOCUMENTS

| | | | |
|---|---|---|---|
| WO | WO 00/27845 A1 | 5/2000 | |
| WO | WO 01/14376 A1 | 3/2001 | |
| WO | WO 01/87853 A1 | 11/2001 | |

* cited by examiner

*Primary Examiner*—Monique T. Cole
(74) *Attorney, Agent, or Firm*—Baerbel R. Brown; Melvin Winokur

(57) ABSTRACT

This invention relates to a process for making spiro isobenzofuranone compounds by coupling of an aminopyrazine fragment with a spirolactone piece.

8 Claims, No Drawings

PROCESS FOR MAKING SPIRO ISOBENZOFURANONE COMPOUNDS

CROSS-REFERENCE TO RELATED APPLICATIONS

This application claims the benefit of U.S. Provisional Application No. 60/263,463, filed Jan. 23, 2001.

BACKGROUND OF THE INVENTION

This invention relates to a process for making spiro isobenzofuranone compounds, in particular 2-oxo-N-(5-phenylpyrazinyl)spiro[isobenzofuran-1(3H),4'-piperidine]-1'-carboxamide by coupling of an aminopyrazine fragment with a spirolactone piece.

For the aminopyrazine fragment, the process in this invention involves a selective monobromination, a catalyzed Suzuki coupling and carbamate formation steps. The synthesis of the spirolactone piece involves lithiation/addition to 1-benzyl-4-piperidone, acid catalyzed cyclization and deprotection by hydrogenolysis. Prior to the present invention, the monobromination of 2-aminopyrazine would produce a low yield of the desired product due to side reactions. However, the use of a flow-cell type reactor in the present invention significantly improves the yield. During the Suzuki coupling, the addition of a stable crystalline solid catalyst with reliable quality improves the coupling. In addition, the present invention provides an environmentally sound process that eliminates the need to use pyridine as the solvent during the carbamate formation and chloroform in the final coupling. As a result, the present invention provides an environmentally sound procedure for making functionalized pyrazine compound in good yields.

SUMMARY OF THE INVENTION

By this invention, there is provided a process for the preparation of a compound of structural formula I:

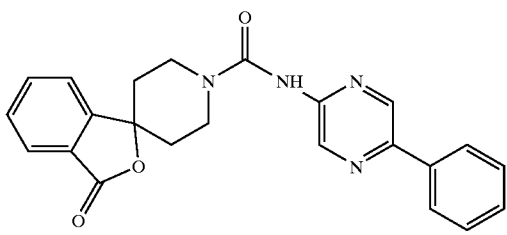

I comprising coupling a compound of formula II with a compound of formula II in the presence of an organic base.

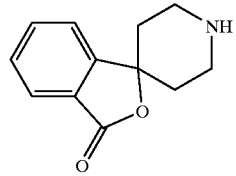

II

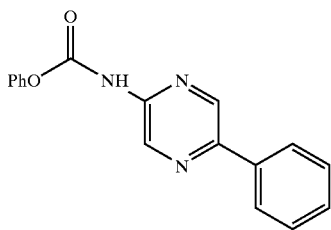

III

The invention is also directed to a process comprising combining 2-amino-5-phenylpyrazine and phenyl chloroformate in a solvent system to yield the compound of formula III.

The invention is also directed to a process comprising the step of combining 2-amino-5-bromopyrazine and phenyl boronic acid in the presence of a catalyst to yield the compound of formula IV.

IV

The invention is also directed to a process comprising the step of combining 2-aminopyrazine and a bromination agent to yield a compound of formula V.

V

DETAILED DESCRIPTION OF THE INVENTION

By this invention, there is provided a process for the preparation of a compound of structural formula I:

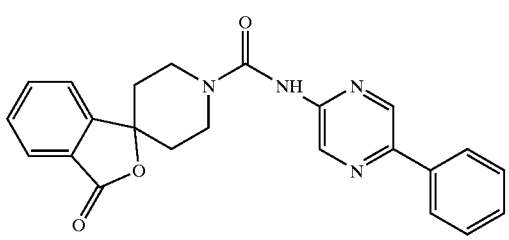

I comprising coupling a compound of formula be with a compound of formula III in the presence of an organic base.

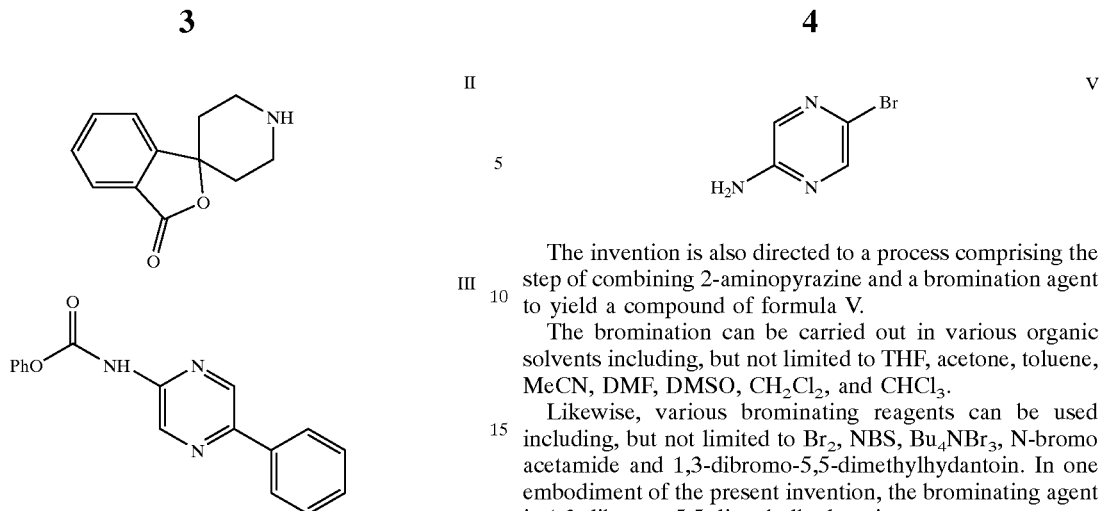

A variety of organic bases can be used to yield compounds of formula I. In one class of the invention, the organic base is a tertiary organic base. In a subclass of the invention, the organic base is selected from triethylamine and i-Pr$_2$NEt.

Various solvent systems can be used to yield compounds of formula I. In one class of the invention, the solvent systems include, but are not limited to MeCN, DMF, DMSO, THF, MeCN/water and DMF/water. In a subclass of the invention, the solvent system is DMF.

The invention is also directed to a process comprising combining 2-amino-5-phenylpyrazine and phenyl chloroformate in an organic solvent system to yield the compound of formula III.

The organic solvent system can include, but is not limited to pyridine, diethyl ether, THF, DMF, MeCN, CH$_2$Cl$_2$ and any mixtures thereof. In a class of the invention, the organic solvent system comprises THF, DMF and MeCN and mixtures thereof.

The invention is also directed to a process comprising the step of combining 2-amino-5-bromopyrazine and phenyl boronic acid in the presence of a catalyst to yield the compound of formula IV.

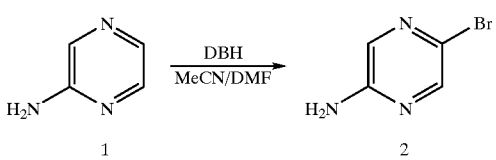

A variety of Palladium catalysts can be used during the Suzuki coupling step to yield IV. Suzuki coupling, a versatile method for synthesizing unsymmetrical biaryl compounds, is a palladium mediated cross coupling reaction of an arylhalide with boronic acid. Generally, Pd(II) catalysts are more active than Pd(0) catalysts. Examples of Palladium catalysts include: PdCl$_2$·dppf·CH$_2$Cl$_2$, Pd(PPh$_3$)$_4$, Pd(OAc)/PPh$_3$, Cl$_2$Pd[(Pet$_3$)]$_2$, Pd(DIPHOS)$_2$, Cl$_2$Pd(Bipy), [PdCl(Ph$_2$PCH$_2$PPh$_2$)]$_2$, Cl$_2$Pd[P(o-tol)$_3$]$_2$, Pd$_2$(dba)$_3$/P(o-tol)$_3$, Pd$_2$(dba)/P(furyl)$_3$, Cl$_2$Pd[P(furyl)$_3$]$_2$, Cl$_2$Pd(PMePh$_2$)$_2$, Cl$_2$Pd[P(4-F-Ph)$_3$]$_2$, Cl$_2$Pd[P(C$_6$F$_6$)$_3$]$_2$, Cl$_2$Pd[P($_2$—COOH-Ph)(Ph)$_2$]$_2$, Cl$_2$Pd[P(4-COOH-Ph)(Ph)$_2$]$_2$. In a class of the invention, the catalyst is selected from PdCl$_2$·dppf·CH$_2$Cl$_2$, Pd(PPh$_3$)$_4$, Cl$_2$Pd[P(4-F-Ph)$_3$]$_2$, Cl$_2$Pd[P(4-CO-OH-Ph)(Ph)$_2$]$_2$. In a subclass of the invention, the catalyst is PdCl$_2$·dppf·CH$_2$Cl$_2$.

The invention is also directed to a process comprising the step of combining 2-aminopyrazine and a bromination agent to yield a compound of formula V.

The bromination can be carried out in various organic solvents including, but not limited to THF, acetone, toluene, MeCN, DMF, DMSO, CH$_2$Cl$_2$, and CHCl$_3$.

Likewise, various brominating reagents can be used including, but not limited to Br$_2$, NBS, Bu$_4$NBr$_3$, N-bromo acetamide and 1,3-dibromo-5,5-dimethylhydantoin. In one embodiment of the present invention, the brominating agent is 1,3-dibromo-5,5-dimethylhydantoin.

In the schemes and examples below, various reagent symbols and abbreviations have the following meanings:

| | |
|---|---|
| Bu$_4$NBr$_3$: | Tetra-N-butyl ammonium bromide |
| CH$_2$Cl$_2$: | Methylene chloride |
| CHCl$_3$: | Chloroform |
| DBH: | 1,3-Dibromo-5,5-dimethylhydantoin |
| DMF: | Dimethylformamide |
| DMSO: | Dimethylsulfoxide |
| EtOAc: | Ethyl acetate |
| IPAC: | Isopropyl acetate |
| MeCN: | Acetonitrile |
| MTBE: | t-Butyl methyl ether |
| NBS: | N-bromo succinamide |
| PhB(OH)$_2$: | Phenyl boronic acid |
| PhOCOCl: | Phenyl chloroformate |
| THF: | Tetrahydrofuran |

EXAMPLE 1

Bromination

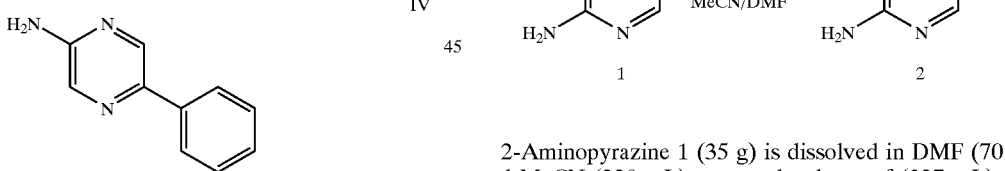

2-Aminopyrazine 1 (35 g) is dissolved in DMF (70 mL) and MeCN (228 mL) to a total volume of (327 mL). Also 1,3-dibromo-5,5-dimethylhydantoin (DBH) (55.2 g) is dissolved into cold (0–5° C.) DMF (35.0 mL) and MeCN (339 mL) to a total volume of 392 mL. To the reactor is added 35 mL MeCN, which is cooled to 0° C. Both the 2-aminopyrazine and the DBH solutions are added simultaneously over 4–6 hours. The reactor temperature is controlled to 0–5° C. The charge rate is ~1.36 mL/min for the 2-aminopyrazine solution and ~1.63 mL/min for the DBH solution. The reaction mixture is aged for 0.5 hours after the complete addition of both solutions. Then, Na$_2$S$_2$O$_3$·5H$_2$O (10%, 70 mL) is added to quench the reaction. Next, the reaction mixture is distilled under reduced pressure to remove the MeCN. The residue volume should be about 220 mL. Na$_2$CO$_3$ (10%, 70 mL) and water (263 mL) are added, followed by Solka-Floc (10.5 g). The mixture is stirred 1 h, then filtered through a Solka-Floc pad to remove precipitate in the crude reaction mixture. The pad is rinsed with 1/2

MeCN/H₂O (60 mL) and the filtrate is saturated with NaCl (100 g). It is then extracted with 3/2 EtOAc/heptane (350 mL, 160 mL×2). The combined organic extract is washed with brine (210 mL, 140 mL×3) then treated with Darco-KB (3.5 g) overnight. It is then filtered through a Solka-Floc pad, and rinsed with 3/2 EtOAc/heptane (70 mL). The filtrate is concentrated to ~17 mL, then flushed with heptane (150–200 mL) until the loss in the supernatant is about 5% (final volume ~200 mL). The product is filtered, washed with 15/1 heptane/EtOAc (100 mL) and dried on the funnel overnight to give the product 2 as a yellow solid. HPLC conditions: ES Industry AQS-C8 4.6×250 mm. A, MeCN; B: 0.1% H₃PO₄; Linear gradient 0 to 96% A in 18 minutes, 35° C.; Flow 1.50 mL/min. RT: 1, 2.6 min, 2, 7.3 min; dibromination, 10.7 min.

Suzuki Coupling

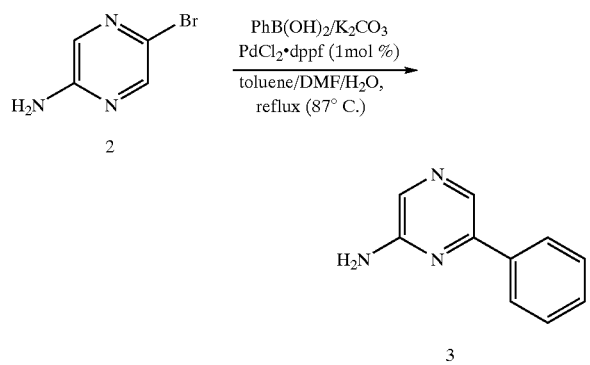

To a 100-mL round bottom flask are added toluene (20 mL), water (20 mL), DMF (4.0 mL), K₂CO₃ (4.77 g), 2-amino-5-bromopyrazine 2 (4.30 g) and phenylboronic acid (3.08 g), followed by the catalyst PdCl₂·dppf·CH₂Cl₂ (84 mg). The mixture is degassed by a vacuum/N₂ cycle three times, then heated to reflux (~87° C.) until the starting material 2 is less than 1A % by HPLC (5–8 h). It is cooled to 25° C., then THF (20 mL) is added to dissolve the product. The organic layer is separated and then washed with brine (20 mL). It is then treated with Darco-KB (600 mg) for 3 hours. The mixture is filtered through a Solka-Floc pad and the filter cake is washed with 1/1 toluene/THF (8.0 mL). The filtrate is concentrated under vacuo to ~16 mL, then heptane (20 mL) is added over ~1 hour and the mixture is aged for 2 hours. The product is collected by filtration and the filter cake is washed with 1/1 toluene/heptane (8.0 mL). It is dried on the funnel to constant weigh affording the product 3 as a yellow solid. HPLC conditions: same as in described in the bromination step. RT: phenylboronic acid, 8.0 min (broad), Suzuki product 3, 9.7 min.

Carbamate Formation

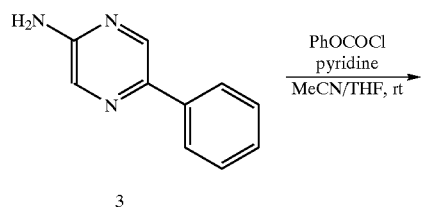

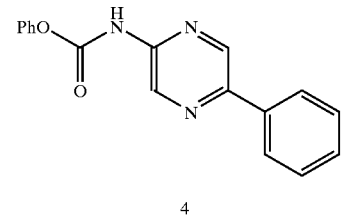

2-Amino-5-phenylpyrazine 3 (3.40 g) is dissolved into a mixture of THF (13.6 mL), MeCN (18.1 mL) and pyridine (1.89 g, 1.93 mL, 1.2 equiv.). Then, phenyl chloroformate (3.27 g, 2.62 mL, 1.05 equiv.) is added slowly (2–4 hour) at 20–30° C. with slight cooling, if necessary. The mixture is stirred for 0.5 hour and the completion of the reaction is confirmed by HPLC. The crystallized product is collected by filtration and the filter cake is washed with 2/1 MeCN/THF (16 mL) and then dried on the funnel in a stream of nitrogen until constant weight is achieved to give the carbamate 4 as a white solid.

HPLC conditions are the same as described in the bromination step. RT: carbamate 4, 14.6 min, phenol, 8.6 min.

1'-Benzylspiro[isobenzofuran-1(3H),4'-piperidin]-3-one Hydrochloride

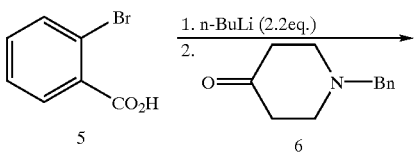

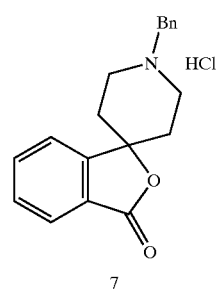

Dry THF (400 mL) and bromobenzoic acid 5 (19.98 g, 99.4 mmol) is charged to a 1-L three neck round RBF under nitrogen. The reaction mixture is cooled to −78° C., then n-butyllithium in hexane (1.52 M, 144 mL, 219 mmol, 2.2 eq.) is added slowly (4–5 hours) with efficient stirring and maintaining the reaction mixture at −71 to −78° C. The mixture is stirred for two more hours.

To a 500 mL RBF are added THF (8.3 ml), 1-benzyl-4-piperidone 6 (22.6 g, 119 mmol, 1.2 eq.) and heptane (52 mL) under nitrogen. The solution is cooled to 0° C. and slowly (50 minutes) added to the aryl lithium solution prepared while maintaining the reaction mixture at −71 to −83° C. It is stirred at −71 to −75° C. for 30 minutes.

The reaction mixture is quenched into a mixture of water (200 mL) and MTBE (160 mL) over 20 min with vigorous stirring. The mixture is stirred at 0–10° C. for 20 minutes. The aqueous layer is separated and treated with concentrate HCl (96 mL, 1.15 mol) and heated to refluxed (72–74° C.) for 4 hours. The mixture is cooled to 14° C. and IPAC (200 mL) is added followed by slow addition of 6N NaOH (161 g, 796 mmol) at 0–10° C. over 1 hour and K₂CO₃ (25.4 g, 184 mmol). The mixture is stirred at 9° C. for 15 min and the organic layer is separated. The organic layer is washed with water (~40 mL×2) and then concentrated to 120 mL at 23–29° C. under reduced pressure. It is then dried by azeotropic distillation with more dry IPAC to KF<675 ppm at 28–40° C. under reduced pressure. More IPAC (124 mL) is added and the mixture is seeded with 36 mg of the HCl salt 7. HCl (4 M in ethyl acetate, 1.00 g) is added with vigorous stirring and the mixture is stirred at 26° C. for 30 minutes to initiate the crystallization. Additional HCl (4 M in ethyl acetate, 14.7 g) is added with vigorous stirring at 26° C. over 45 minutes. The batch is aged overnight at 26–28° C. and filtered to give 17.56 g of compound 7 as white crystals after drying (53.6% yield).

Spiro[isobenzofuran-1(3H),4'-piperidin]-3-one hydrochloride monohydrate

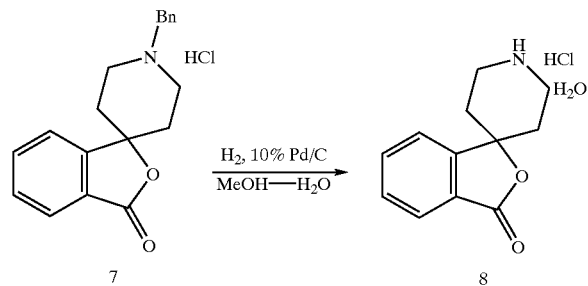

A mixture of water (41 mL), methanol (410 mL), and 7 (25.6 g, 77.6 mmol) and 10% Pd/C (50% wet, 5.12 g) is hydrogenated at 28–31° C. (0.16–0.20 MPa) for 4 hours. The catalyst is filtered off and the filtrate is concentrated to 80 mL at 29–59° C. under reduced pressure. It is then partially dried by flushing with MeOH at 41–56° C. until KF<500 ppm. The mixture is heated to 54° C. to dissolve the product then cooled to 26° C. in 2 hours and aged for 30 minutes to crystallize the product. MTBE (45.4 g) was slowly added and the slurry is aged for 30 min. Additional MTBE (159 g) was added in 30 minutes and the supernatant is sampled to check KF to be within spec. (1.5%<KF<2%). The slurry is aged overnight at 26° C. and the crystal is confirmed to be monohydrate by X-ray and KF (KF, 6–8 w %). The product is filtered and washed with methanol/MTBE (1/5, 41 mL×2) and dried under reduced pressure at 22–27° C. for 22 hours to give 18.2 g of product 8, 91% yield, 99.82A %.

Final Coupling

8

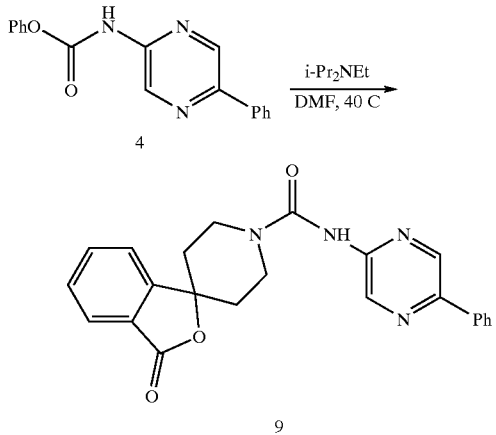

Spirolactone.HCl salt monohydrate 8 (4.56 g) is added to a solution of i-Pr₂NEt (2.66 g, 3.59 mL) in DMF (35 mL). The slurry is stirred for 0.5 hour and then the carbamate 4 (5.00 g) is added. The mixture is degassed once by a vacuum/N₂ cycle and then heated to 40–45° C. After aging at 45° C. for 2 hour and confirming the completion of the reaction by HPLC, the reaction mixture is cooled to 20–25° C., then quenched with AcOH (0.30 mL).

The reaction mixture is filtered to remove any extraneous solid. Water (10.5 mL) is added and the mixture is aged for three hours, more water (12.8 mL) is added slowly (2–4 hours). After aging overnight, the crystal form is checked to be type D by x-ray and the loss in the supernatant is checked by HPLC (<3 mg/mL). The solid is collected by filtration and the filter cake is washed with 1/1 DMF/H₂O (20 mL), then water (20 mL). It is dried in a stream of nitrogen until constant weight is achieved to give the type D crystal (6.7 g). It is slurried in MeCN (20 mL) for 6 hours to convert it into form B crystals. After confirming the conversion, the solid is filtered, rinsed with MeCN (3.5 mL) and dried under vacuum with a stream of nitrogen until constant weight is achieved to give the product 9 as a white solid.

HPLC conditions are identical to those described in bromination step. RT: spirolactone, 5.6 min; carbamate 14.6 min; L-753,550, 14.1 min.

What is claimed is:

1. A process for preparing a compound of formula I:

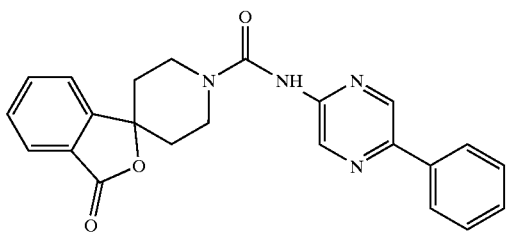

comprising coupling a compound of formula II with a compound of formula III in the presence of an organic base selected from the group consisting of NBu₃, Me₂NBu and Me₂NBn in a solvent system selected from the group consisting of MeCN, MeCN/water and DMF/water

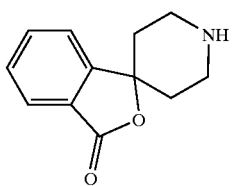

II

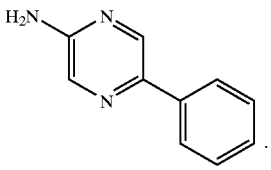

III

2. The process of claim 1 further comprising the step of combining 2-amino-5-phenylpyrazine (IV) and phenyl chloroformate in MeNC to yield the compound of formula III.

3. The process for preparing a compound of formula III of claim 2 further comprising the step of combining 2-amino-5-bromopyrazine (V) and phenyl boronic acid in the presence of a catalyst to yield the compound of formula IV.

IV

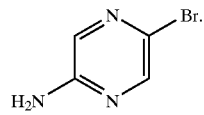

4. The process of claim 3 wherein the catalyst is selected from the group consisting of $PdCl_2 \cdot dppf \cdot CH_2Cl_2$, $Pd(PPh_3)_4$, $Pd(OAc)/PPh_3$, $Cl_2Pd[(Pet_3)]_2$, $Pd(DIPHOS)_2$, $Cl_2Pd(Bipy)$, $[PdCl(Ph_2PCH_2PPh_2)]_2$, $Cl_2Pd[P(o\text{-tol})_3]_2$, $Pd_2(dba)_3/P(o\text{-tol})_3$, $Pd_2(dba)/P(furyl)_3$, $Cl_2Pd[P(furyl)_3]_2$, $Cl_2Pd(PMePh_2)_2$, $Cl_2Pd[P(4\text{-F-Ph})_3]_2$, $Cl_2Pd[P(C_6F_6)_3]_2$, $Cl_2Pd[P(2\text{—COOH-Ph})(Ph)_2]_2$, $Cl_2Pd[P(4\text{-COOH-Ph})(Ph)_2]_2$.

5. The process of claim 4 wherein the catalyst is selected from the group consisting of $PdCl_2 \cdot dppf \cdot CH_2Cl_2$, $Pd(PPh_3)_4$, $Cl_2Pd[P(4\text{-F-Ph})_3]_2$, $Cl_2Pd[P(4\text{-COOH-Ph})(Ph)_2]_2$.

6. The process of claim 3 further comprising the step of combining 2-aminopyrazine and a bromination agent to yield the compound of formula V

V

7. The process of claim 6 wherein the bromination agent is selected from the group consisting of $Br_2$, NBS, $Bu_4NBr_3$, N-bromo acetamide and 1,3-dibromo-5,5-dimethylhydantoin.

8. The process of claim 7 wherein the bromination agent is selected from the group consisting of NBS and 1,3-dibromo-5,5-dimethylhydantoin.

* * * * *